US008994937B2

(12) United States Patent
Mourey et al.

(10) Patent No.: US 8,994,937 B2
(45) Date of Patent: Mar. 31, 2015

(54) SURFACE ENHANCED RAMAN SPECTROSCOPY CALIBRATION CURVE GENERATING SYSTEMS

(75) Inventors: Devin Alexander Mourey, Albany, OR (US); James William Stasiak, Lebanon, OR (US); Zhiyong Li, Foster City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 395 days.

(21) Appl. No.: 13/449,612

(22) Filed: Apr. 18, 2012

(65) Prior Publication Data

US 2013/0278928 A1 Oct. 24, 2013

(51) Int. Cl.
*G01J 3/44* (2006.01)
*G01N 21/27* (2006.01)
*G01N 21/65* (2006.01)

(52) U.S. Cl.
CPC ............ *G01N 21/274* (2013.01); *G01N 21/278* (2013.01); *G01N 21/658* (2013.01)
USPC ......................................................... 356/301

(58) Field of Classification Search
None
See application file for complete search history.

(56) References Cited

U.S. PATENT DOCUMENTS

| | | | |
|---|---|---|---|
| 5,090,806 A * | 2/1992 | Pierce ............................. | 356/301 |
| 7,521,254 B2 | 4/2009 | Pryce-Lewis et al. | |
| 7,604,953 B2 | 10/2009 | Porter et al. | |
| 7,787,117 B1 | 8/2010 | Leona et al. | |
| 7,879,625 B1 | 2/2011 | Boss | |
| 7,898,658 B2 | 3/2011 | Moskovits et al. | |
| 7,973,926 B1 | 7/2011 | Uibel et al. | |
| 2005/0230272 A1* | 10/2005 | Lee et al. ....................... | 205/792 |
| 2007/0155020 A1* | 7/2007 | Su et al. ......................... | 436/518 |
| 2009/0123910 A1 | 5/2009 | Malick et al. | |
| 2011/0026019 A1* | 2/2011 | Tyagi et al. .................... | 356/301 |
| 2011/0069308 A1 | 3/2011 | Zhao et al. | |
| 2011/0116089 A1* | 5/2011 | Schmidt et al. ............... | 356/301 |
| 2011/0231899 A1* | 9/2011 | Pulier et al. ........................ | 726/1 |
| 2012/0075378 A1* | 3/2012 | Baldy et al. ...................... | 347/19 |
| 2012/0212732 A1* | 8/2012 | Santori et al. ................. | 356/301 |

OTHER PUBLICATIONS

Peters, K., "HP'S New Direct Digital Titration Solution", SBS Mar. 2011, 19 pages.

* cited by examiner

*Primary Examiner* — Abdullahi Nur
*Assistant Examiner* — Hina F Ayub
(74) *Attorney, Agent, or Firm* — Dierker & Associates, P.C.

(57) ABSTRACT

A surface enhanced Raman spectroscopy calibration curve generating system includes a SERS sensor, which includes a substrate and a plurality of sensing members formed on the substrate. Each of the sensing members includes a plurality of SERS signal amplifying structures. An inkjet dispensing device is to dispense different concentrations of a solution including a known analyte of interest onto the respective sensing members to form a concentration dependent array. A Raman spectrometer is to interrogate the concentration dependent array. A processor is operatively connected to each of the inkjet dispensing device and the Raman spectrometer. Computer-readable instructions are embedded on a non-transitory, tangible computer-readable medium and are executable by the processor. The computer-readable instructions are to automatically generate an intensity profile as a function of concentration for the concentration dependent array.

16 Claims, 4 Drawing Sheets

SURFACE ENHANCED RAMAN SPECTROSCOPY CALIBRATION CURVE GENERATING SYSTEMS

BACKGROUND

Assays and other sensing systems have been used in the chemical, biochemical, medical and environmental fields to detect the presence and/or concentration of one or more chemical species. Some sensing techniques utilize color or contrast for species detection and measurement, including, for example, those techniques based upon reflectance, transmittance, fluorescence, or phosphorescence. Other sensing techniques, such as Raman spectroscopy or surface enhanced Raman spectroscopy (SERS), study vibrational, rotational, and other low-frequency modes in a system. In particular, Raman spectroscopy is used to study the transitions between molecular energy states when photons interact with molecules, which results in the energy of the scattered photons being shifted. The Raman scattering of a molecule can be seen as two processes. The molecule, which is at a certain energy state, is first excited into another (either virtual or real) energy state by the incident photons, which is ordinarily in the optical frequency domain. The excited molecule then radiates as a dipole source under the influence of the environment in which it sits at a frequency that may be relatively low (i.e., Stokes scattering), or that may be relatively high (i.e., anti-Stokes scattering) compared to the excitation photons. The Raman spectrum of different molecules or matters has characteristic peaks that can be used to identify the species.

BRIEF DESCRIPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

The present disclosure relates generally to surface enhanced Raman spectroscopy concentration calibration curves. Examples of the systems and methods disclosed herein enable the efficient generation of SERS concentration calibration curves at the point of testing a solution. The system(s) incorporate both an inkjet dispenser and a SERS sensing system. The inkjet dispenser is able to quickly and reliably dispense small volumes of different known concentrations of a solution containing a known analyte into different sensing members of a SERS substrate. SERS data obtained from the SERS substrate is concentration dependent, and thus may be used to automatically develop a concentration calibration curve for the known analyte. The SERS substrate containing the different known concentrations may also be used to rapidly and automatically identify the concentration of unknown analytes. As such, the methods disclosed herein use an automatic inkjet dispenser to carry out the calibration process for quantitative analysis of an analyte based on SERS.

The system(s) and method(s) disclosed herein also obviate the need for manually generated calibration curves and look up tables in order to determine the concentration of trace unknown analytes in sample solutions. The systems and methods disclosed herein may also improve the measurement accuracy by minimizing the variation due to, for example, sample uniformity, test environment and conditions, device drifting, etc.

Figure 1:
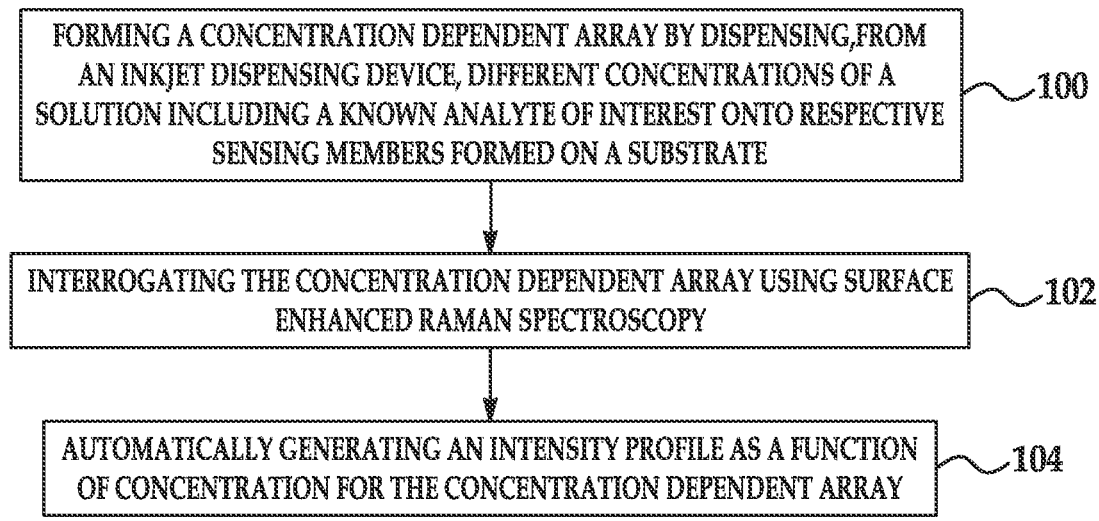
FIG. 1 is a flow diagram of an example of a method for forming a surface enhanced Raman spectroscopy (SERS) concentration calibration curve.

FIG. 1 is a flow diagram depicting an example of the method for forming a SERS concentration calibration curve. As shown at reference numeral 100 in FIG. 1, a concentration dependent array is formed by dispensing, from an inkjet dispensing device, different concentrations of a solution including a known analyte of interest onto respective sensing members formed on a substrate. As shown at reference numeral 102, the concentration dependent array is interrogated using surface enhanced Raman spectroscopy. An intensity profile as a function of concentration for the concentration dependent array is automatically generated, as shown at reference numeral 104. It is to be understood that this example of the method and other examples of the method will be described further herein in reference to the various figures.

Figure 2:
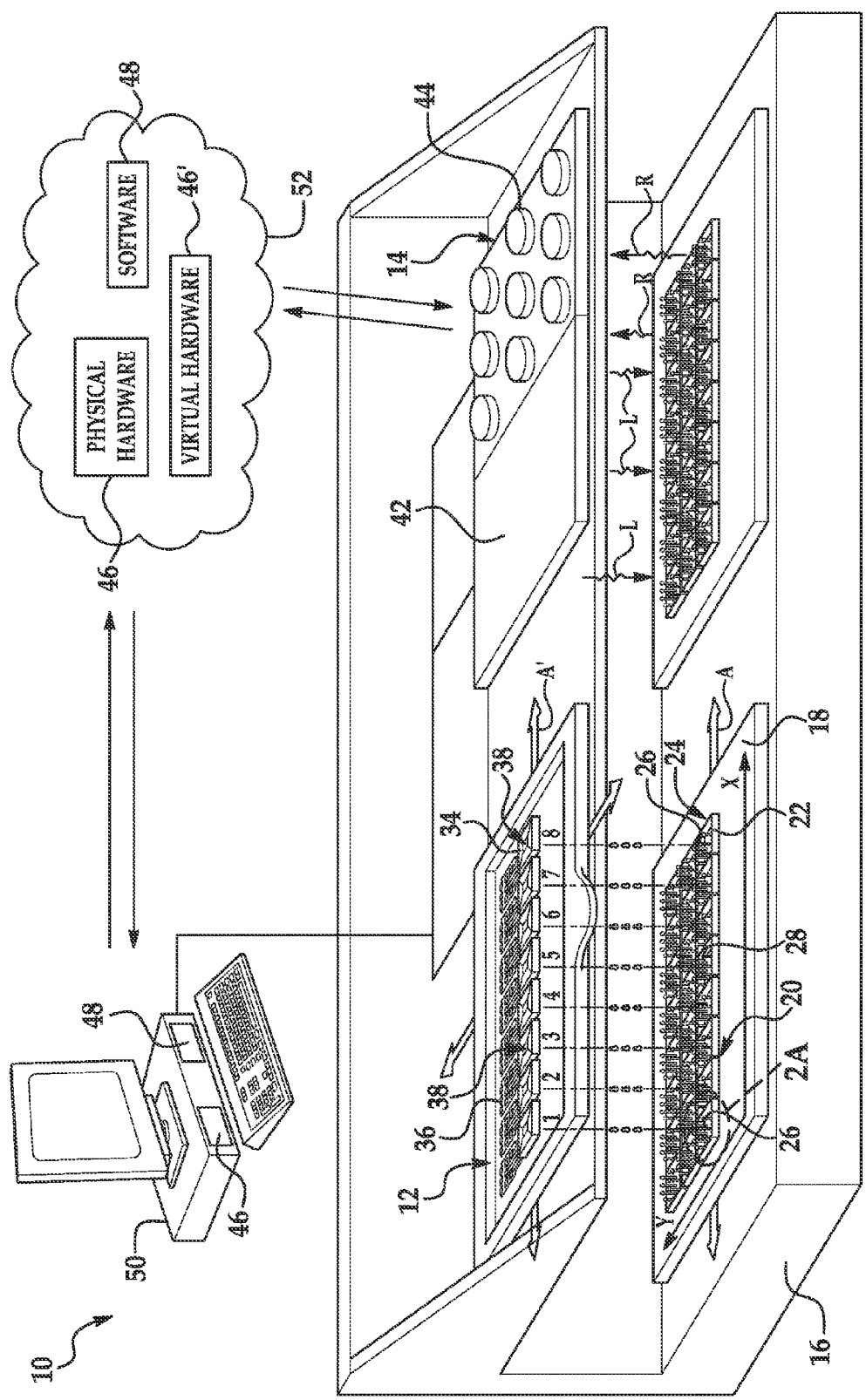
FIG. 2 is semi-schematic, partially perspective view of an example of an integrated SERS concentration calibration curve generating system.

Referring now to FIG. 2, an example of a SERS concentration calibration curve generating system 10 is depicted. In this example, the inkjet dispensing device 12 and the Raman spectrometer 14 are integrated into a single system which includes a housing 16.

As shown in FIG. 2, the housing 16 includes a transport stage 18 that supports a SERS sensor 20. The transport stage 18 may be translated along the lateral axis A to position the SERS sensor 20 for dispensing or SERS interrogation. It is to be understood that the system 10 includes hardware and/or associated programming that are utilized to position the transport stage 18 in an automated fashion.

The SERS sensor 20 includes a substrate 22 having an array of sensing members 24 formed in or on the substrate 22. In the example of FIG. 2, each sensing member 24 includes a well 26 and a plurality of SERS signal amplifying structures 28 positioned in the well 26.

The substrate 22 may be formed of reflective and/or non-reflective materials. Examples of suitable substrate materials include germanium, silicon, glass, quartz, nitrides, alumina, sapphire, indium tin oxide, polymers (e.g., polycarbonate, polyimide, acrylic, polyethylene terephthalate (PET), polypropylene, polyethylene naphthalate (PEN), polyethylene, polyether ether ketone (PEEK), etc.), combinations thereof, and/or layers thereof. When the sensing member 24 includes the well 26 (as shown in FIG. 2), the substrate 22 may also be selected from a material that is capable of having the well 26 formed therein, e.g., via etching, imprinting, embossing, thermoforming, injection molding, or another suitable technique.

The substrate 22 may have any desirable dimensions. The length and width of the substrate 22 are generally large enough to have a desired number of sensing members 24 formed thereon/therein. In an example, the substrate 22 may resemble a 96-well plate, having 96 sensing members 24 formed thereon/therein.

The thickness of the substrate 22 shown in FIG. 2 may be over 100 μm thick to retain structural integrity. In an example, the well 26 formed in the substrate 22 has a depth that ranges from about 1 μm to about 100 μm. As an example, a well 26 having a depth of about 10 μm with a 1 mm×1 mm opening has a volume of about 10 nL. As another example, a well 26 having a depth of about 1 μm with a 100 μm×100 μm opening has a volume of about 10 pL. A typical laser spot on a compact SERS sensor may be about 100 μm, and thus a well opening within the give range may be suitable in order to tolerate any focus/stage movement errors.

Figure 6:
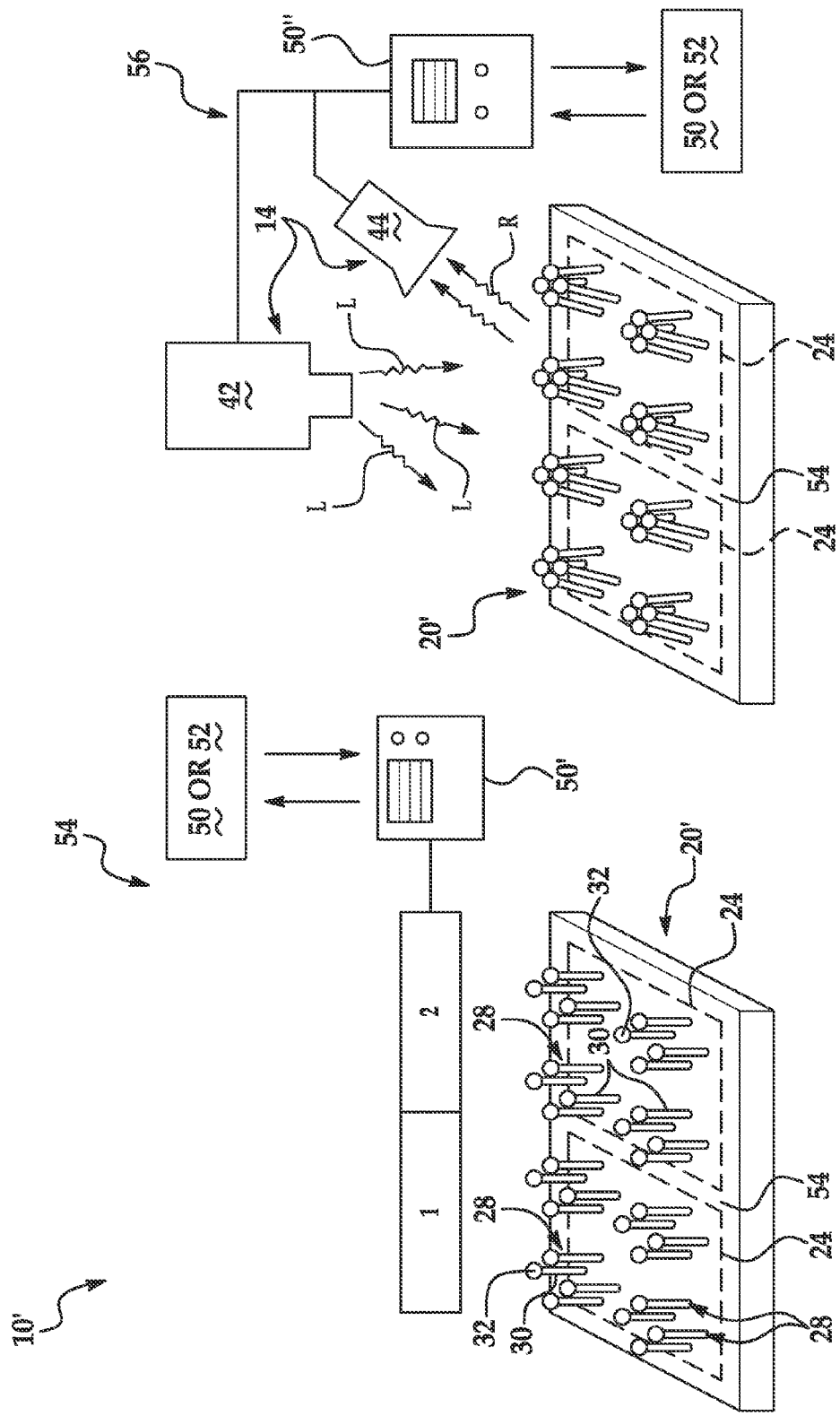
FIG. 6 is a schematic, partially perspective view of an example of a SERS concentration calibration curve generating system having a separate inkjet dispensing system and SERS sensing system.

In the example shown in FIG. 2, the well 26 of each sensing member 24 is a cavity that extends from a surface of the substrate 22 into the substrate 22 to a desirable depth that is less than the thickness of the substrate 22. These cavities may be etched into the substrate 22 to the desired depth. In other examples, the well 26 of each sensing member 24 includes walls that extend from a surface of the substrate 22 above the substrate 22 to a desirable height. In still other examples, the sensing members 24 may not include the well 26, but rather may include a space on the substrate surface that isolates the signal amplifying structures 28 of one sensing member 24 from the signal amplifying structures 28 of adjacent sensing members 24. An example of this type of SERS sensor 20' is shown in FIG. 6.

Figure 2A:
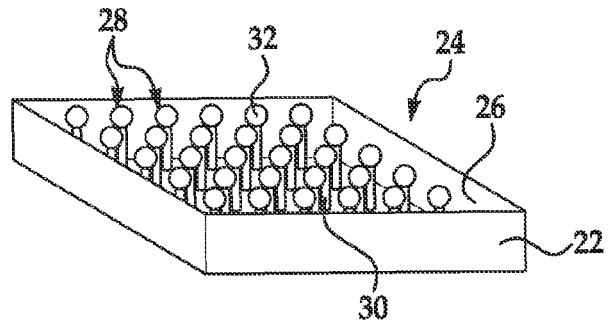
FIG. 2A is a semi-schematic, enlarged, perspective view of an example of one sensing member of the SERS sensor shown in FIG. 2.

FIG. 2A is an enlarged view of one of the sensing members 24 that includes a well 26 and signal amplifying structures 28 formed in the well 26. As such, both FIGS. 2 and 2A may be referenced in the discussion of the sensing members 24.

The wells 26 may be formed to have any desirable shape (e.g., as the well 26 appears from the top view) and may have any desirable dimensions (e.g., length, width, diameter, etc.). Each dimension of the well 26 depends, at least in part, on the type and number of signal amplifying structures 28 to be formed in the wells 26, the number of wells 26 to be formed, and the size of the substrate 22. The example wells 26 shown in FIGS. 2 and 2A have a square shape that continues throughout the depth of the wells 26 or throughout the height of the wells 26. Another suitable shape for the well 26 is a circular or hexagonal shape that continues throughout the depth or height of the well 26. Alternatively, the walls of the wells 26 may be tapered so that the dimensions of the well 26 increase toward the surface of the substrate 22, or increase moving away from the surface of the substrate 22 when walls are formed on the surface. In an example, the dimensions of each well 26 may be selected to be 1 mm by 1 mm. This would enable SERS interrogation to take place in one well 26 at a time if that were desirable.

As illustrated in FIG. 2, the wells 26 are fluidically isolated from one another so that each well 26 may receive a different concentration of the known analyte solution without well to well contamination or mixing. Techniques for forming the wells 26 will be discussed in more detail below.

As mentioned above, each sensing member 24 includes the signal amplifying structure(s) 28 positioned in the wells 26. The type and number of signal amplifying structures 28 that are used may depend, at least in part, upon the dimensions of the well 26. As illustrated in FIGS. 2 and 2A, the signal amplifying structures 28 include a nano-structure base 30 and a signal amplifying material 32 positioned on at least a portion of the nano-structure base 30. Examples of nano-structure bases 30 include antennas, pillars or nano-wires, poles, flexible columnar or finger-like structures, nanoflake structures, mushroom-shaped nano-structures, cone-shaped structures, multi-faceted structures, etc. Some examples of the signal amplifying structures 28 (e.g., pillars, flexible columnar or finger-like structure, nano-flakes, mushroom-shaped nano-structures, etc.) are collapsible signal amplifying structures that are able to undergo self-coalescence (e.g., self-closing at their tips), with the aid of capillary forces (e.g., during liquid evaporation). The collapsible signal amplifying structures are able to trap analytes at hot spots formed among the closed tips, which greatly amplifies electromagnetic fields under SERS interrogation and improves uniformity and reliability of hot spot formation. Analytes tend to concentrate at or near the tips of non-collapsible signal amplifying structures (e.g., antenna, cones, etc.) which also greatly amplifies electromagnetic fields under SERS interrogation.

The signal amplifying material 32 may be any material that is capable of enhancing the SERS signal that is generated during surface enhanced Raman spectroscopy. In an example, the signal amplifying material 32 is a material that increases the number of Raman scattered photons when the analyte (or other species of interest) is trapped by, or is otherwise concentrated at or near, the signal amplifying structure(s) 28, and when the analyte and material 32 are subjected to light/electromagnetic radiation. Raman signal-enhancing materials include, but are not limited to, silver, gold, and copper.

The signal amplifying structures 28 may be formed into a multi-structure assembly, such as a dimer (i.e., 2 structures), trimer (i.e., 3 structures), tetramer (i.e., 4 structures, see FIG. 6), pentamer (i.e., 5 structures 18), etc., or they may be randomly positioned within the wells 26.

The SERS sensor 20 may be formed via a number of methods. In particular, the wells 26 may be formed via any suitable technique, which depends, at least in part, upon the type of substrate 22 used, and whether it is desirable to sequentially or simultaneously form the wells 26 and signal amplifying structure(s) 28.

In an example method, the signal amplifying structures 28 and wells 26 are formed sequentially. In this example method, a two-step masking and etching process may be used. For example, a mask that provides the desired pattern for the signal amplifying structures 28 may be placed on the substrate 22 and etching may be performed to a desired depth that is less than the thickness of the substrate 22 and less than or equal to the desired depth for the well(s) 26. While the etchant used will depend upon the substrate material that is being used, this step will generally involve an isotropic (wet or dry) etching process. After the signal amplifying structure(s) 28 are formed by depositing suitable materials, the mask will be removed. Another mask that provides the desired pattern for the wells 26 while protecting the previously formed signal amplifying structure(s) 28 may be placed on the substrate 22. This etching step may be performed to a desired depth that is less than the thickness of the substrate 22 and less than or equal to the height of the previously formed signal amplifying structure(s) 28.

In another example method, the signal amplifying structure(s) 28 and wells 26 are formed simultaneously. In this example, a mold may be used to form both the nano-structure bases 30 of the signal amplifying structure(s) 28 and the wells 26. The mold may be formed of single crystalline silicon, polymeric materials (acrylics, polycarbonates, polydimethylsiloxane (PDMS), polyimide, etc.), metals (aluminum, copper, stainless steel, nickel, alloys, etc.), quartz, ceramic, sapphire, silicon nitride, or glass. The mold includes a negative replica pattern of the desired signal amplifying structures 28 and wells 26, and thus defines the shapes for at least the bases 30 of the signal amplifying structure(s) 28 and for the wells 26 that are to be formed. The negative replica pattern may be of any of the nano-structures previously mentioned. The pattern for the signal amplifying structures 28 in different wells 26 may all be the same (e.g., all pillars), may all be different (e.g., pillars, poles, finger-like structures, etc.), or the pattern for some of the signal amplifying structures 28 may be different in some of the wells 26. Still further, when multiple wells 26 are formed using the same mold, the pattern for the wells 26 may be the same or different for at least one of the wells 26.

The negative replica pattern may be integrally formed in the mold. In an example, the pattern may be formed in the mold via deep reactive ion etching and passivation. More specifically, the Bosch process may be used, and this process involves a series of alternating cycles of etching (e.g., using $SF_6$ and $O_2$ plasmas) and passivation (e.g., using a $C_4F_8$ plasma). The morphology of the resulting pattern may be controlled by controlling the conditions (e.g., vacuum pressure, RF power, total processing time, individual etching cycle time, individual passivation cycle time, and gas flow rates) of the process. In an example, the etcher may be operated at a pressure of 15 mTorr, the coil and platen powers of the etcher are 800 W and 10 W, respectively, each etching cycle (with $SF_6$ and $O_2$) is 6 seconds, each passivation cycle (with $C_4F_8$) is 5 seconds, and the flow rates for $SF_6$, $O_2$, and $C_4F_8$ are 100 sccm, 13 sccm, and 100 sccm, respectively. More generally, the flow rate may be any rate up to about 100 sccm.

The portion of the negative replica pattern that forms the signal amplifying structure(s) 28 may include a regular or non-regular array of the nano-structure base shapes. The etching and passivation process previously described often results in a non-regular array. It is to be understood that in order to generate a regular array (e.g., the tetramers shown in FIG. 6), a fabrication method, such as focused ion-beam lithography, electron beam (i.e., e-beam) lithography, or optical lithography may be used.

The mold may be pressed into the substrate 22 or a coating on the substrate 22, which in this example, is a resin material. Alternatively, the resin material can be deposited (e.g., via spin coating, drop coating, dip-coating, or the like) on the mold. In the latter example, when the resin material is to be a coating on the substrate 22, the substrate 22 may be adhered to the resin material while the resin material is deposited on the mold, or after the resin material is removed from the mold. The resin material may be an ultraviolet (UV) curable resin material or a thermally curable resin material. While the mold is pressed into (or otherwise in contact with) the resin material, the structure may be exposed to UV light or heat in order to partially or fully cure the resin material substrate. It is to be understood that the time for UV or heat exposure, the power of the UV lamp used, the temperature of the heat, and other like curing parameters will depend, at least in part, on the resin material that is used.

Once curing is complete, the mold may be removed, and the resulting structure includes the cured substrate 22 or a cured resin material (adhered to, or to be adhered to the substrate 22) patterned to form the wells 26 and the bases 30 of the signal amplifying structure(s) 28. While the mold is pressed into (or otherwise in contact with) the resin material substrate, partial curing may be performed. Partial curing cures some, but not all, of the resin material. After partial curing, the mold may be removed. Once the mold is removed, curing may be continued until the resin material is fully cured.

In this example method, once curing is complete and the mold is removed, the signal-enhancing material 32 is deposited on at least a surface of the nano-structure bases 30 to form the signal amplifying structure(s) 28. The signal-enhancing material 32 may be established by any suitable deposition or other coating technique. In some examples, a selective deposition technique may be used so that the material 32 is established on, for example, the tips of the nano-structure bases 30 alone. As examples, the material 32 may be deposited via electron-beam (e-beam) evaporation or sputtering. In still other examples, the signal-enhancing material 32 can be pre-formed nanoparticles (e.g., of silver, gold, copper, etc.), which are coated onto the nano-structure bases 30. Such nanoparticles may have an average diameter ranging from about 10 nm to about 100 nm. It is believed that the presence of the material 32 nanoparticles at the apex of the nano-structure bases 30 further enhances the electric field during, e.g., a SERS operation. The material 32 itself may also have a surface roughness that spontaneously forms during the deposition process. This surface roughness can act as additional optical antennas to increases the SERS-active sites over each signal amplifying structure 38.

In another example method, a desirable well and structure pattern may be formed in a first mold (e.g., silicon) which is used to form the reverse pattern in a daughter polymer mold. The daughter mold is then used as described above to form the desired pattern in a curable resin. Furthermore, any of the methods disclosed herein may be used to form the SERS substrate 20' that does not include wells 26. For example, the mold would include a replica (when multiple molds are used) or a negative replica (when a single mold is used) of the signal amplifying structures, without a pattern for a well.

It is to be understood that the previously described method(s) may be implemented as a roll-to-roll process.

Referring back to FIG. 2, the SERS concentration calibration curve generating system 10 also includes the inkjet dispensing device 12. In the example shown in FIG. 2, the inkjet dispensing device 12 is a cassette with any number of dispensing units, eight of which are shown and labeled 1-8. While this example of the inkjet dispensing device 12 includes a single row of dispensing units, the device 12 may be configured with multiple rows and columns of dispensing units to facilitate simultaneous dispensing to multiple rows and columns of corresponding sensing members 24.

Each dispensing unit 1-8 includes a die (positioned beneath the cassette and thus not shown) with attached fluid extenders 34 and attached addressing circuitry 36 (electrical leads, traces, pins, and contact pads). In this example, a monolithically integrated die defines all of the dispensing units 1-8, including the associated fluid channels 38. Each of the fluid channels 38 includes an actuator (not shown) operatively positioned therein. Example actuators include thermal jet actuators, piezo jet actuators, or piezo-capillary jet actuators. The actuators may be aligned with one or more nozzles so that when actuated, droplets of a predetermined volume may be dispensed from the fluid channel 38 into the well 26 (or otherwise onto the sensing member 24) of the SERS sensor 20 (or SERS sensor 20').

Solutions containing known analytes may be introduced into the fluid channels 38 via another fluid dispenser (e.g., a pipette), a fluid source (e.g., where fluid is drawn into the channel 38), or a reservoir (e.g., which delivers the fluid/ substance on command to the fluid channel(s) 38 in response to signals from hardware and/or associated programming.

The inkjet dispensing device 12 may be translated along the axis A' that is parallel to the lateral axis A and or along the axis A" that is perpendicular to the lateral axis A. The system 10 is capable of moving the inkjet dispensing device 12 along either or both axes A', A" to position the inkjet dispensing device 12 adjacent to the SERS sensor 20 to dispense the solutions into the wells 26 according to a predefined layout. In an example, the inkjet dispensing device 12 is capable of dispensing the solution(s) at a rate of at least 15 pL per second. In another example, the rate of dispensing ranges from about 15 pL per second to about 1 µL per second. It is to be understood that the system 10 includes hardware and/or associated programming that are utilized to position the inkjet dispensing device 12 in an automated fashion, and to individually actuate the dispensing units 1-8 in an automated fashion. The dispensing units 1-8 may be controlled to dispense solution(s) simultaneously (e.g., to an entire row at the same time), individually (e.g., to each sensing member 24 one at a time), and/or sequentially (e.g., to one row, and then another row, etc.).

Figure 3:
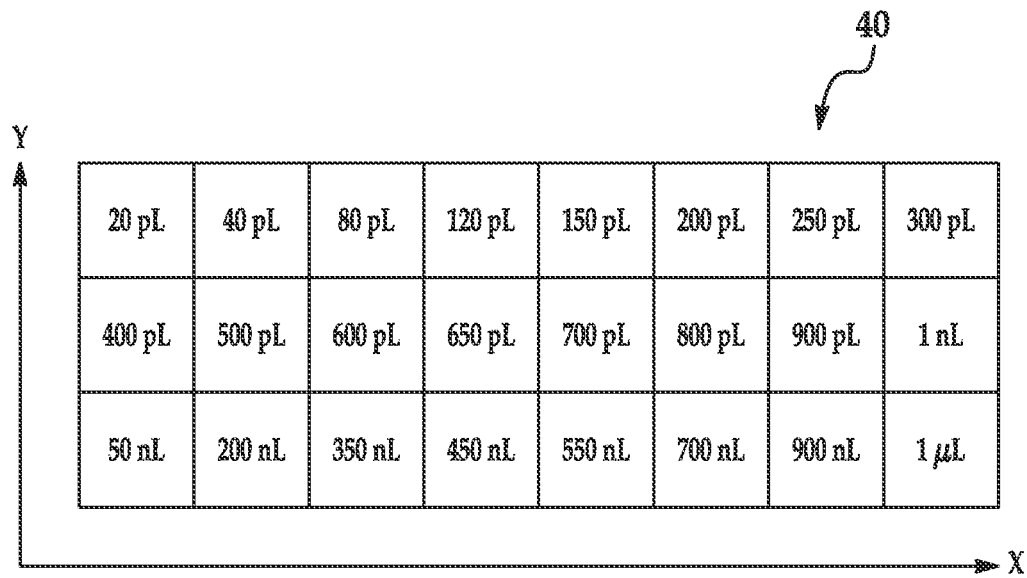
FIG. 3 is a schematic depiction of an example layout for dispensing different known concentrations of a solution containing a known analyte into different sensing members of the SERS substrate shown in FIG. 2.

An example of a predefined layout 40 is shown in FIG. 3. This layout 40 corresponds with the SERS sensor 20 shown in FIG. 2. Hardware, programming, or combinations thereof may be used to create the dispensing layouts 40. A user may be offered multiple layout choices (e.g., on a screen of a computing device), and he/she may input his/her choices via, for example, an input device, such as a keyboard or keypad, mouse, touchscreen, etc. The layout choices may include the number of sensing members 24 in the SERS sensor 20 to be used, the position of the SERS sensor 20 on the transport stage 18, and the amount of fluid to be dispensed from each dispensing unit 1-8 into each well 26 of each sensing member 24.

In an example, the user may identify the position of the SERS sensor 20 with respect to the X and Y axes of the transport stage 18 as well as the number of sensing members 24 in each row and column of the SERS sensor 20. The user may then be presented with a blank layout that can be infilled with information about the fluid amount that is to be dispensed. The fluid amounts depend, at least in part, upon the desired concentration calibration curve that is to be generated and upon the type of known solution that is used. As one example, different drop amounts may be input into the blank layout when the known solution is a single solution with a set concentration (e.g., a solution containing 1 mM melamine). As another example, the same drop amount may be input into the blank layout when different known solutions having different concentrations of the analyte (e.g., solutions including 1 mM melamine, 1 nM melamine, 1 µM melamine, etc.) are to be utilized. FIG. 3 illustrates a layout 40 in which the dispensing amounts have been identified. The inkjet dispensing device 12 will dispense the known solution(s) into the respective wells 26 of the SERS sensor 20 (or onto respective sensing members 24 of SERS sensor 20') according to the layout 40. Referring back to FIG. 2, each dispensing unit 1-8 may be positioned and actuated to dispense the solution(s) to each row according to the layout 40.

The SERS concentration calibration curve generating system 10 of FIG. 2 also includes the Raman spectrometer 14, which includes a laser source 42 and a detector 44. When it is desirable to perform a sensing operation, the transport stage 18 that supports the SERS sensor 20 may be translated along the lateral axis A to position the SERS sensor 20 adjacent to the laser source 42 and the detector 44.

The laser source 42 may be a light source that has a narrow spectral line width, and is selected to emit monochromatic light beams L within the visible range or within the near-infrared range. The positioning of the light source 42 with respect to the inkjet dispensing device 12 may be far enough to enable dispensed droplets to begin evaporation. The positioning of the components will be dependent upon the architecture of the system 10, but in an example, the light source 42 may be from about 1 cm to about 2 cm from the inkjet dispensing device 12. The laser source 42 may be selected from a steady state laser or a pulsed laser. The laser source 42 is positioned to project the light L onto the various sensing members 24.

The example shown in FIG. 2 may be a VCSEL (vertical cavity surface emitting light) array that includes a multiplexing component that is able to sort out the SERS signals emitted from each of the members 24. In other examples, the laser source 42 may be selected to interrogate a single sensing member 24 at a time, or multiple rows or columns of sensing members 24 at the same time. As such, parallel sensing may be performed. A lens (not shown) and/or other optical equipment (e.g., optical microscope) may be used to direct (e.g., bend) the laser light L in a desired manner. In one example, the laser source 42 is integrated on a chip.

The detector 40 may be any photodetector that is capable of optically filtering out any reflected components and/or Rayleigh components and then detecting an intensity of the Raman scattered radiation R for each wavelength near an incident wavelength.

The laser source 42 and the detector may also be operatively connected to a power supply (not shown).

While not shown, it is to be understood that the system 10 may include a light filtering element positioned between the sensing members 24 and the photodetector 44. This light filtering element may be used to optically filter out any Rayleigh components, and/or any of the Raman scattered radiation R that is not of a desired region. The system 10 may also include a light dispersion element positioned between the sensing members 24 and the photodetector 44. The light dispersion element may cause the Raman scattered radiation R to be dispersed at different angles. The light filtering and light dispersion elements may be part of the same device or may be separate devices.

During one example of the operation of the system 10, the dispensing units 1-8 may be filled with the same solution that has a known concentration of a known analyte. In this example, the dispensing units 1-8 may then be actuated to dispense different amounts of the single solution onto the different sensing members 24 according to a predefined layout 40. Dispensing various numbers of drops (e.g., 1, 100, 1000, 100,000, etc.) of the same solution into each of the sensing members 24 varies the concentration of the known analyte by orders of magnitude across the SERS sensor 20.

During another example of the operation of the system 10, the dispensing units 1-8 may be filled with the different solutions, each of which has a different, but known, concentration of a known analyte. In this example, the dispensing units 1-8 may then be actuated to dispense the same amount of different solutions onto the different sensing members 24 according to a predefined layout 40. Different amounts of each of the different solutions may also be dispensed (e.g., into different rows) in order to further vary the concentrations of each of the different solutions. Using solutions with different concentrations may be desirable to achieve a wider concentration range (e.g., 1 mM, 1 µM, etc.) across the SERS sensor 20.

During still another example of the operation of the system 10, all but one of the dispensing units 1-8 may be filled with the same solution that has a known concentration of a known analyte, or all but one of the dispensing units 1-8 may be filled with different solutions, each of which has a different but known concentration of a known analyte. In this example, the sensing members 24 of the SERS sensor 20 may also be partially or fully filled with an unknown solution containing an unknown analyte(s). The SERS sensor 20 may be pre-partially or fully filled by dipping the SERS sensor 20 into the unknown solution, by jetting the unknown solution from the dispensing units 1-8, or by pipetting or otherwise dispensing the unknown solution into/onto each of the sensing members 24. As noted above, when an unknown solution is being analyzed, it is desirable to keep one of the sensing members 24 free of the solution including the known analyte (i.e., the solution including the known analyte is not dispensed into one of the sensing members 24).

Each of the previously described dispensing schemes forms a concentration dependent array of the solution(s) including the known analyte across the sensing members 24 of the SERS sensor 20. After the known solution(s), and in some examples the unknown solution, are added to the sensing members 24, the transport stage 18 may be translated to align the SERS sensor 20 with the Raman spectrometer 14. As the SERS sensor 20 is moved, the dispensed solution(s) begin to evaporate, thereby concentrating the analyte(s) at or near the signal amplifying structures 28, or collapsing the signal amplifying structures 28 and capturing the analytes in the collapsed structures. The system 10 may include an integrated heater (e.g., between the inkjet dispensing device 12 and the Raman spectrometer 14) to assist in drying the solution(s) and increasing droplet mobility. The integrated heater may be, for example, a resistive type heating device or a thermoelectric type heating device. In an example, the heating device is integrated with a thermocouple to measure the temperature, with active control circuitry, and with a power supply.

When sensing members 24 that have received the solution(s) are adjacent to the light source 42, the laser source 42 is operated to emit light L toward the respective sensing members 24. The analyte molecules trapped in, or concentrated at or near the signal amplifying structures 28 of the sensing members 24 interact with and scatter the light/electromagnetic radiation L (note that the scattered light/electromagnetic radiation is labeled R). The interactions between the analyte molecules and the signal amplifying material 32 of the signal amplifying structures 28 cause an increase in the strength of the Raman scattered radiation R. The Raman scattered radiation R is redirected toward the photodetector 44, which, as noted above, may optically filter out any reflected components and/or Rayleigh components and then detect an intensity of the Raman scattered radiation R for each wavelength near the incident wavelength. It is to be understood that the Raman spectrometer 14 may be operated to scan across the entire SERS sensor 20.

Figure 4:
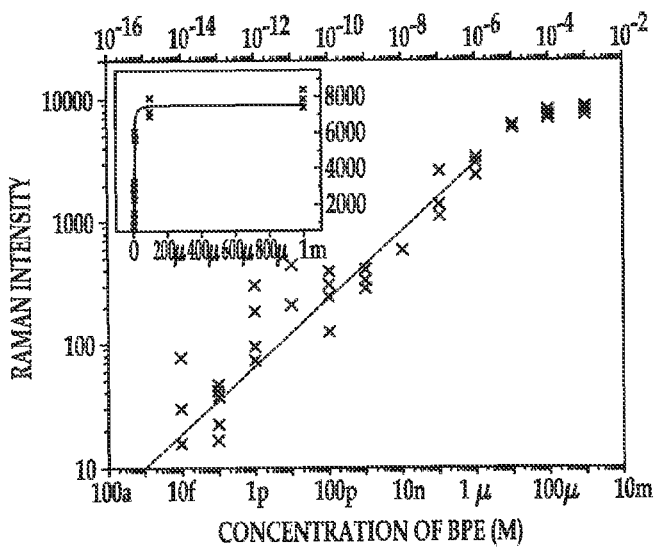
FIG. 4 is a graph depicting an intensity profile as a function of concentration for a solution including a known analyte.
Figure 5:
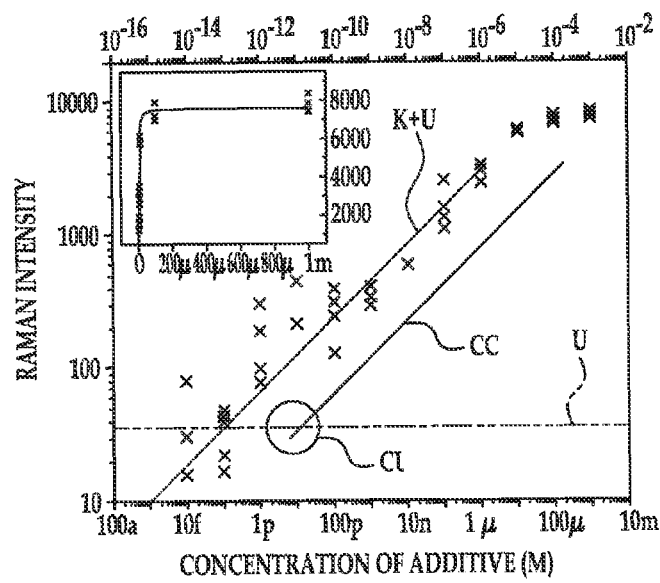
FIG. 5 is a graph depicting i) an intensity profile as a function of concentration for a solution including an unknown analyte that is mixed with a solution including a known concentration of a known analyte, ii) an intensity signal of the solution including the unknown analyte without the solution including the known concentration of the known analyte, and iii) a calculated intensity profile as a function of concentration for the solution including the unknown analyte.

When the Raman interrogation is complete, hardware and/or associated programming (which will be described further hereinbelow) that is capable of analyzing the data receives the concentration data and the Raman data and causes a concentration calibration curve to be generated. The concentration calibration curves depict the measured Raman intensity as a function of the concentration for the particular concentration dependent array then-currently being analyzed. FIGS. 4 and 5 illustrate examples of the graphs that may be generated. More particularly, FIG. 4 illustrates an example of a concentration calibration curve that may be generated for a concentration dependent array created without an unknown solution, and FIG. 5 illustrates an example of a concentration calibration curve that may be generated for a concentration dependent array that also includes the unknown solution.

Referring now to FIG. 4, a concentration calibration curve is shown that may be generated for trans-1,2-bis(4-pyridyl)ethylene (BPE). To obtain this curve, different droplet amounts of a solution containing a known concentration of BPE may be dispensed into or onto respective sensing members 24 of the SERS sensor 20. Alternatively, to obtain this curve, the same amount of droplets of different solutions containing different known concentrations of BPE may be dispensed into or onto respective sensing members 24 of the SERS sensor 20. As illustrated, multiple SERS intensity signals are measured for each of the sensing members 24 (e.g., at 10 femtoliters, at 1 picoliter, at 100 picoliters, etc.), and then a fitted function is generated for the data. As an example, this function can be determined by a least squared linear regression of the logarithm of the Raman intensity and the logarithm of the analyte concentration. In the example shown in FIG. 4, the plot is on a log-log scale to produce the fitted curve that is shown. The inset of the graph shows more detail at the higher concentrations and higher intensities.

As noted above, the results shown in FIG. 5 are obtained when the concentration dependent array of the known solution containing the known analyte is mixed with an unknown solution containing unknown analyte(s). In this example, the known analyte is also trans-1,2-bis(4-pyridyl)ethylene (BPE). To obtain these results, the sensing members 24 of the SERS sensor 20 are at least partially filled will the unknown solution. The known solution(s) containing the known analyte may be dispensed into the sensing members 24 according to either of the methods previously described. In this example, one of the sensing members 24 contains the unknown solution without having any of the known solution added thereto. The other sensing members 24 have a mixture of the unknown solution and different concentrations of the known solution. The data from this type of concentration dependent array includes Raman intensity signals from the unknown solution that is not mixed with the known solution (see line "U" in FIG. 5), and Raman intensity signals from the various mixtures of unknown solution and the known solution (the fitted line/curve for which is labeled "K+U" in FIG. 5). The inset of the graph shows more detail at the higher concentrations and higher intensities for the curve K+U.

The hardware and/or associated programming that is capable of analyzing the data is capable of determining the concentration calibration curve of the unknown analyte in the unknown solution by subtracting the intensity of the unknown solution U from the fitted curve K+U for the mixed solutions. The calculated concentration calibration curve for the unknown solution is labeled "CC" in FIG. 5. The generation of this curve CC allows many undesirable background signals in the unknown solution to be subtracted out. The concentration of the unknown in the unknown solution may be determined by identifying the point at which the line U intersects with the calculated concentration calibration curve for the unknown solution CC. This point, which is indicative of the estimated concentration of the analyte in the unknown solution, is circled and labeled CU in FIG. 5.

The concentration calibration curves disclosed herein may be created at the point of test. This enables a user to identify a fitted line or curve for the Raman intensities that result when using a particular solution and a particular SERS sensor 20. This may be advantageous because different intensities at different peaks may result for the same sample, for example, due to different analyte interactions taking place with the Raman-enhancing material 32 as well as other environmental factors. The concentration calibration curve enable one to account for these unique properties for the particular test being run, and thus enables a user to perform quantitative analysis in addition to any qualitative analysis.

In foregoing discussion, various components have been described as combinations of hardware, programming, or combinations thereof. These components may be implemented in a variety of fashions. Referring back to FIG. 2, hardware 46, 46' and associated programming 48 may be operatively connected to the inkjet dispensing device 12, the laser source 42 and the photodetector 44 in order to control these components. The same or different hardware 46, 46' may receive the concentration information (e.g., in the form of the layout 40), may receive readings from the photodetector 44, and may cause the same or different associated programming 48 to produce concentration calibration curves (such as shown shown in FIGS. 4 and 5). In this example, the hardware 46, 46' may include any processor that can execute computer-readable instructions for generating concentration calibration curves and associated data from Raman intensity data and concentration data, and memory device(s) that can store data transmitted thereto for subsequent retrieval, analysis, creation of a database or library, etc.

The hardware 46 and associated programming 48 may be part of a computing device 50 that is directly connected to the components 12, 42, 44. In an example, the programming 48 (e.g., computer-readable instructions) may be part of an installation package that can be executed by the processor of the computing device 50. In these instances, the memory may be a portable medium, such as a compact disc (CD), a digital video disc (DVD), or a flash drive, or the memory may be a memory maintained by a server from which the installation package can be downloaded and installed on the computing system 50. In another example, the program instructions may be part of an application or applications already installed on the computing system 50. In this other example, the memory may include integrated memory, such as a hard drive. In still other examples, the memory media may integrated in the same device 50 as the processor, or it may be separate from, but accessible to that device 50 and processor.

Additionally or alternatively, hardware 46 and associated programming 48 may be part of a cloud computing system 52. Local hardware 46 and associated programming 48 that are part of the computing system 50 may be desirable to operate the dispensing device 12 and the Raman spectrometer 14, and the cloud computing system 52 may be desirable for data generation, data storage, and for performing analytical applications with such data.

The cloud computing system 52 is a computing system that includes multiple pieces of hardware 46, 46' operatively coupled over a network so that they can perform a specific computing task (e.g., running the system 10 components, receiving concentration information from the computing system 50 and Raman data from the detector 44, enabling multiple users to access and/or manipulate stored concentration data, SERS data, etc. via the cloud 52). The cloud hardware may include a combination of physical hardware 46 (e.g., processors, servers, memory, etc.), software (i.e., associated programming 48), and virtual hardware 46'. In an example, the cloud 52 may be configured to (i) receive requests from a multiplicity of users through application client devices (such as computing device 50), and (ii) return request responses. In the examples disclosed herein, the requests may relate to retrieval of SERS concentration calibration data, building of a SERS concentration calibration library utilizing stored data, etc.

Physical hardware 46 may include processors, memory devices, and networking equipment. Virtual hardware 46' is a type of software that is processed by physical hardware 46 and designed to emulate specific hardware. For example, virtual hardware 46' may include a virtual machine, i.e. a software implementation of a computer that supports execution of an application like a physical machine. An application, as used herein, refers to a set of specific instructions executable by a computing system for facilitating carrying out a specific task. For example, an application may take the form of a web-based tool providing users with a specific functionality, e.g., retrieving previously saved SERS concentration calibration data. Software 48 is a set of instructions and data configured to cause virtual hardware 46' to execute an application. As such, the cloud 52 can make a particular application related to the sensing system 10 available to users through client devices 50.

The computing device 50 may be any personal computer, portable computer, content server, a network PC, a personal digital assistant (PDA), a cellular telephone or any other computing device that is capable of performing the functions for receiving input from and/or providing control or driving output to the various devices (e.g., 12, 14), performing desired programming, and/or contenting to the cloud computing system 52 in order to perform the desired programming.

Referring now to FIG. 6, another example of a SERS calibration curve generating system 10' is depicted. In this example, the inkjet dispensing device 12 and the Raman spectrometer 14 are separate systems, namely an inkjet system 54 and a Raman system 56. These devices 12, 14 may be the same as devices 12, 14 previously described.

Each of the separate systems 54, 56 in this example includes its own computing device 50', 50". The computing device 50' of the inkjet system 54 includes hardware 46 and programming 48 at least to control the inkjet dispensing device 12 and to transmit concentration data to another computing device 50 or to the cloud computing system 52. The computing device 50" of the Raman system 56 includes hardware 46 and programming 48 at least to control the Raman spectrometer 14 and to transmit intensity data to another computing device 50 or to the cloud computing system 52.

In the example of FIG. 6, the other computing device 50 or the cloud 52 includes hardware 46, 46' and associated programming 48 that is capable of receiving the concentration layout information from the computing system 50' of the inkjet system 54 and the SERS data from the computing system 50" of the Raman system 56. The hardware 46, 46' and associated programming 48 of the other computing device 50 or the cloud 52 is capable of automatically generating the concentration calibration curve(s) and any other associated data disclosed herein.

The SERS sensor 20' illustrated in FIG. 6 includes sensing members 24 that are not separated by the walls of wells 26, but rather have a space 54 that physically separates the signal amplifying structures 28 of one sensing member 24 from another sensing member 24. This example of the SERS sensor 20' also includes collapsible signal amplifying structures 28 that when exposed to analyte solutions collapse to trap the analytes between adjacent structures 28 (as shown in the sensor 20' positioned adjacent to the Raman spectrometer 14).

When using the system 10', the SERS sensor 20' is positioned within the inkjet system 54 adjacent to the inkjet dispensing device 12 in order to receive dispensed solution(s) to form the concentrated dependent array of the known analyte solution according to an example disclosed herein. In some instances, an unknown solution may also be introduced onto the SERS sensor 20' as previously described. In this example, dispensing to individual sensing members 24 may be desirable to allow for drying so that the different concentrations remain separated. After dispensing is accomplished, the SERS sensor 20' is physically moved into an operable position in the Raman system 56 adjacent to the Raman spectrometer 14 where SERS interrogation takes place.

The data from each of the computing systems 50', 50" is transmitted to the shared local computing system 50 or the shared cloud computing system 52 so that concentration calibration curve generation can take place.

The systems 10, 10' shown in FIGS. 2 and 6 may also include mechanisms that induce mixing within the sensing members 24. As an example, mixing may be accomplished using the same mechanical fixture that is used in FIG. 2 to transfer the substrate 22 in proximity of the spectrometer 14.

It is to be understood that the ranges provided herein include the stated range and any value or sub-range within the stated range. For example, a range from about 15 pL per second to about 1 µL per second should be interpreted to include not only the explicitly recited limits of about 15 pL per second to about 1 µL per second, but also to include individual values, such as 500 pL, 275 nL, 550 nL, etc., and sub-ranges, such as from about 50 pL to about 750 nL, from about 500 pL to about 500 nL, etc. Furthermore, when "about" is utilized to describe a value, this is meant to encompass minor variations (up to +/−10%) from the stated value.

While several examples have been described in detail, it will be apparent to those skilled in the art that the disclosed examples may be modified. Therefore, the foregoing description is to be considered non-limiting.

What is claimed is:

1. A surface enhanced Raman spectroscopy (SERS) calibration curve generating system, comprising:
    a SERS sensor, including:
        a substrate; and
        a plurality of sensing members formed on the substrate, each of the sensing members including a plurality of SERS signal amplifying structures;
    an inkjet dispensing device to dispense different concentrations of a solution including a known analyte of interest onto the respective sensing members to form a concentration dependent array;
    an unknown solution to be introduced to at least partially cover at least some of the plurality of SERS signal amplifying structures prior to forming the concentration dependent array;
    a Raman spectrometer to interrogate the concentration dependent array;
    a processor operatively connected to each of the inkjet dispensing device and the Raman spectrometer; and
    computer-readable instructions embedded on a non-transitory, tangible computer-readable medium and executable by the processor, the computer-readable instructions to automatically generate an intensity profile as a function of concentration for the concentration dependent array.

2. The system as defined in claim 1 wherein the plurality of SERS signal amplifying structures includes collapsible nanopillars having a SERS signal amplifying material deposited on a portion thereof.

3. The system as defined in claim 1 wherein the inkjet dispensing device, the Raman spectrometer, and the processor are integrated into a single system.

4. The system as defined in claim 1 wherein the processor is operatively connected to a cloud computing system that is to receive the generated intensity profile as the function of concentration for the concentration dependent array.

5. The system as defined in claim 1, further comprising computer-readable instructions to cause the inkjet dispensing device to dispense the different concentrations by:
    i) dispensing a predetermined number of drops on one of the respective sensing members, and automatically increasing the predetermined number of drops dispensed on each other respective sensing member, and drying each of the predetermined number of drops; or
    ii) dispensing multiple samples of the solution including the known analyte of interest, each of the multiple samples including a different concentration of the known analyte of interest.

6. A method for forming a surface enhanced Raman spectroscopy (SERS) concentration calibration curve, comprising:
    at least partially covering a plurality of SERS signal amplifying structures of each respective sensing member formed on a substrate with an unknown solution prior to forming a concentration dependent array;
    forming the concentration dependent array by dispensing, from an inkjet dispensing device, different concentrations of a solution including a known analyte of interest onto the respective sensing members;
    when forming the concentration dependent array, dispensing the solution including the known analyte of interest such that one of the respective sensing members does not receive the solution including the known analyte of interest;
    interrogating the concentration dependent array using surface enhanced Raman spectroscopy; and
    automatically generating, by a processor executing computer-readable instructions embedded on a non-transitory, tangible computer-readable medium, an intensity profile as a function of concentration for the concentration dependent array.

7. The method as defined in claim 6, further comprising:
    automatically generating, by the processor, a fitted function for the intensity profile as the function of concentration for the concentration dependent array; and
    automatically determining, by the processor, a concentration of the known analyte in the unknown solution by subtracting an intensity of the unknown solution on the respective sensing member that does not receive the solution including the known analyte of interest from the fitted function.

8. The method as defined in claim 6 wherein the dispensing of the different concentrations is achieved by:
    dispensing, from the inkjet dispensing device, a predetermined number of drops on one of the respective sensing members;
    automatically increasing the predetermined number of drops dispensed on each other respective sensing member; and
    drying each of the predetermined number of drops to obtain the different concentrations.

9. The method as defined in claim 6 wherein the dispensing of the different concentrations is achieved by dispensing, from the inkjet dispensing device, multiple samples of the solution including the known analyte of interest, each of the multiple samples including a different concentration of the known analyte of interest.

10. The method as defined in claim 9 wherein the multiple samples are dispensed onto the respective sensing members simultaneously.

11. The method as defined in claim 6 wherein a rate of the dispensing is at least 15 pL per second.

12. The method as defined in claim 6, further comprising:
   transmitting the SERS concentration calibration curve to a cloud computing system; and
   storing the SERS concentration calibration curve on a memory device of the cloud computing system.

13. The method as defined in claim 12, further comprising generating a library of SERS concentration calibration curves for a variety of known analytes based upon SERS concentration calibration curves received at the cloud computing system.

14. The method as defined in claim 6, further comprising drying the dispensed solution prior to interrogating the concentration dependent array.

15. The method as defined in claim 6 wherein the processor is operatively connected to the inkjet dispensing system, and wherein the method further comprises one of:
   receiving, at the processor, signal intensity data for the concentration dependent array from a Raman spectrometer that is integrated into a system with the inkjet dispensing system; or
   receiving, at the processor, signal intensity data for the concentration dependent array from a separate Raman spectrometer that is operatively connected to the processor.

16. A non-transitory, tangible computer readable medium having instructions embedded thereon that when executed implement a method for forming a surface enhanced Raman spectroscopy (SERS) concentration calibration curve, the method comprising:
   causing a plurality of SERS signal amplifying structures of each respective sensing member formed on a substrate to be at least partially covered with an unknown solution prior to forming a concentration dependent array;
   causing the concentration dependent array to be formed by causing an inkjet dispensing device to dispense different concentrations of a solution including a known analyte of interest onto the respective sensing members;
   when forming the concentration dependent array, causing the solution including the known analyte of interest to be dispensed such that one of the respective sensing members does not receive the solution including the known analyte of interest;
   causing a surface enhanced Raman spectroscopy interrogation of the concentration dependent array; and
   automatically generating an intensity profile as a function of concentration for the concentration dependent array.

* * * * *